United States Patent [19]

Naylor

[11] Patent Number: 5,093,244
[45] Date of Patent: Mar. 3, 1992

[54] PRODUCTION OF A DEOXYRIBONUCLEOSIDE

[75] Inventor: Linda A. Naylor, Durham, England

[73] Assignee: Imperial Chemical Industries PLC, London, England

[21] Appl. No.: 354,726

[22] Filed: May 22, 1989

[30] Foreign Application Priority Data

May 31, 1988 [GB] United Kingdom ............... 8812846
Mar. 22, 1989 [GB] United Kingdom ............... 8906623

[51] Int. Cl.$^5$ .................. C12P 19/38; C12P 19/26; C12P 19/30; C07H 15/12
[52] U.S. Cl. ........................ 435/87; 435/84; 435/85; 435/89; 435/803; 435/840; 536/22; 536/23; 536/29; 536/124; 536/127
[58] Field of Search .............. 435/85, 87, 89, 840, 435/803; 536/24, 26, 27, 28, 29

[56] References Cited

U.S. PATENT DOCUMENTS 3,249,511  5/1966  Okumura et al. .................. 435/92
3,444,040  5/1969  Nara et al. ......................... 435/92
3,586,604  6/1971  Yamanoi et al. ................... 435/92
3,912,587  10/1975  Enei et al. ........................ 435/88

FOREIGN PATENT DOCUMENTS 2126437  10/1972  France ............................. 435/87

Primary Examiner—Robert A. Wax
Assistant Examiner—Stephanie W. Zitomer
Attorney, Agent, or Firm—Cushman, Darby & Cushman

[57] ABSTRACT

A process for the fermentative production of the deoxyribonucleoside thymidine and/or its corresponding base thymine by aerobically cultivating a strain of the genus Brevibacterium, in particular one of the strains NCIMB 40117 and 40116. The produced thymidine may be used as an intermediate in the production of azidothymidine and active ingredient in a composition for use in the treatment of auto imune deficiency syndrome (AIDS). Biologically pure cultures of strain NCIMB 40014 and variants and mutants derived therefrom are claimed per se.

11 Claims, No Drawings

PRODUCTION OF A DEOXYRIBONUCLEOSIDE

PRODUCTION OF A DEOXYRIBONUCLEOSIDE

This invention relates to a process for the production of the deoxyribonucleoside thymidine and/or its corresponding base thymine.

Thymidine mono-phosphate (TMP) is a nucleotide formed by all microorganisms during DNA production. The corresponding nucleoside thymidine is an intermediate in the production of azidothymidine the active ingredient in a composition for use in the treatment of auto immune deficiency syndrome (AIDS). Thymidine is a pyrimidine nucleoside and at present is produced chemically although fermentative production of a polysaccharide containing thymidine with a mutant strain of *Bacilus subtilis* has been suggested in Japanese Patent Publication No. 39-16345, published 11 Aug. 1964. Neither the mutant strain used nor the strain from which it was derived appears to have been deposited in a recognised culture collection and the mutant strain is only identified in Publication No. 39-16345 as mutant strain 2901. There appears to be no fermentation process at present for production of thymidine or thymine per se. In addition to pyrimidine nucleosides there are nucleosides of the purine class. Production of a corresponding nucleotide of the purine class, guanosine-5'-monophosphate, by fermentation using a strain of *Brevibacterium helvolum* has been suggested in U.S. Pat. No. 3,249,511 published 3 May 1966.

According to the present invention we provide a process for the production of thymidine and/or thymine which comprises aerobically cultivating a thymidine and/or thymine producing bacterial strain of the genus Brevibacterium in a culture medium containing an assimilable carbon source and other nutrients under suitable cultural conditions, accumulating the produced thymidine and/or thymine directly in the medium and thereafter separating the produced and accumulated thymidine and/or thymine from the medium.

Any suitable strain of the genus Brevibacterium may be used in the process of the invention but thymidine and/or thymine producing strains of *Brevibacterium helvolum* are preferred.

A particularly suitable strain is strain 431 derived from *Brevibacterium helvolum* ATCC 19390 by the method described in detail in Example 1 of this specification. ATCC 19390 is mentioned in U.S. Pat. No. 3,586,606 which describes a process for producing ribotides of 2-substituted-6-hydroxypurines by fermentation. A culture of strain 431 has been deposited at the National Collections of Industrial and Marine Bacteria Ltd. (NCIMB), PO Box 31, 135 Abbey Road, Aberdeen, AB9 8DG, Scotland, United Kingdom on 28 Apr. 1988 and has been given the accession number NCIMB 40014.

Further strains which are particularly suitable are *Brevibacterium helvolum* strains L-17 (derived from strain NCIMB 40014) and 2.977 (derived from strain ATCC 19390), L-17 being derived as described in Example 3 of this specification and 2.977 being derived by a method essentially the same as that used to derive L-17. Cultures of L-17 and 2.977 have been deposited at NCIMB on 21 Feb. 1989 and have been given the accession numbers 40117 and 40116 respectively.

Also according to the present invention we provide biologically pure cultures of *Brevibacterium helvolum* strain NCIMB 40014 and variants and mutants derived therefrom.

Biologically pure cultures of *Brevibacterium helvolum* strains NCIMB 40117 and 40116 and variants and mutants derived therefrom are inventive subjects defined in our co-pending UK Patent Application No. 8906624.5 filed on 22 Mar. 1989.

The process of the invention is most effective when carried out as a fed batch or batch process but continuous methods are possible. Preferably the carbon source is glucose but other carbon sources such as other sugars and alcohols can be used. Preferably the pH is in the range 5 to 9, particularly 6 to 8 with a pH at or near 7 being especially suitable. A base such as ammonium hydroxide can be added to the culture medium to maintain the pH at the required level. Suitably the temperature is in the range 20° to 35° C. with temperatures in the range 25° to 30° C. being preferred. A particularly suitable production medium for the process of the invention is set out in Table 1.

TABLE 1

| Component | Concentration per l |
|---|---|
| yeast extract | 10.0 g |
| MgSO$_4$.7H$_2$O | 2.0 g |
| K$_2$SO$_4$ | 2.0 g |
| trisodium citrate | 0.5 g |
| CaCl$_2$ | 0.55 g |
| FeSO$_4$.7H$_2$O | 0.1 g |
| MnSO$_4$.4H$_2$O | 16.2 mg |
| ZnSO$_4$.7H$_2$O | 44.0 mg |
| CuSO$_4$ | 8.0 mg |
| Co(NO$_3$)$_2$ | 0.5 ml |
| Na molybdate.2H$_2$O | 1.0 mg |
| Thiamine | 5.0 mg |
| Calcium pantothenate | 10.0 mg |
| Biotin | 1.0 mg |
| Folic acid | 50.0 mg |
| H$_3$PO$_4$ | 50.0 ml. |
| Glucose | to give 150 g |

Another suitable production medium for the proces of the invention is set out in Table 2.

TABLE 2

| Component | Concentration per l |
|---|---|
| yeast extract | 10 g |
| MgSO$_4$.7H$_2$O | 1 g |
| K$_2$SO$_4$ | 1 g |
| trisodium citrate | 0.5 g |
| FeSO$_4$.7H$_2$O | 0.1 g |
| Trace elements Mixture (Fisons Co) | 20 ml. |
| Thiamine | 5 mg |
| Calcium pantothenate | 10 mg |
| Biotin | 30 mg |
| Folic acid | .05 g |
| H$_3$PO$_4$ | 25 ml. |
| Glucose | 50 g |

After production and accumulation of the thymidine and/or thymine it may be separated from the supernatant liquid in the culture by any suitable means for example ion exchange, liquid extraction and hydrophobic chromatography, ion exchange being preferred. A suitable ion exchange separation procedure for thymidine and/or thymine is to adsorb these solutes onto an ion exchange resin and to elute the thymidine and/or thymine specifically using water and methanol.

The produced thymidine can be used in the production of azidothymidine and other medical and biochemical drug products.

The invention is illustrated by the following examples:

EXAMPLE 1

Production of Strain 431 (NCIMB 40014)

Strain 431 was produced by a 3-stage method from ATCC 19390. In a first stage ATCC 19390 was treated with UV light to the resulting culture was added the pyrimidine analogue 5-fluoro-uracil. Cells were then selected which were 5-fluoro-uracil resistant producing strain 190. Strain 190 was thereafter cultured and treated with UV light followed by 5-fluoro-uracil and 5-fluoro-uracil resistant cells were again selected to produce strain 295. Strain 295 was treated with UV light and thereafter cells were selected which showed decreased growth on thymidine as sole carbon source. This selection produced strain 431. Strain 431 shows a marked ability to produce thymidine and/or thymine which products accumulate in the culture medium.

EXAMPLE 2

Production of Thymidine Using Strain 431

The inoculation medium set out in Table 2 was prepared and was inoculated in a shake flask with a culture of strain Brevibacterium 431 produced as described in Example 1.

TABLE 3

| Component | Concentration per l |
| --- | --- |
| $K_2HPO_4$ | 10.5 g |
| $KH_2PO_4$ | 4.5 g |
| $(NH_4)_2SO_4$ | 1 g |
| trisodium citrate $2H_2O$ | 0.5 g |
| $MgSO_4.7H_2O$ | 0.5 ml. |

The inoculated medium was shaken using a stirrer speed of 150 rpm at a temperature of 28° C. and a pH of 7. 200 mls of the inoculated medium were thereafter transferred to a fermenter having a 4 liter working volume and the medium set out in Table 1 was added. Cultivation then took place at a pH of 7 (maintained by additions of 50% ammonium hydoxide solution), a temperature of 30° C. and under a zero dissolved oxygen tension (DOT). A stirrer speed of 500 rpm was maintained during cultivation. During cultivation the glucose concentration in the medium was monitored and when it fell to a concentration below 5 g/l further glucose was added to bring the concentration up to 50 g/l. 0.26 g/l of thymidine and 2.6 g/l of thymine were produced after 7 days fermentation, the products being identified by high performance liquid chromatography (H.P.L.C).

EXAMPLE 3

Production of Strain L-17

Strain L-17 was produced from strain NCIMB 40014 by treating a culture of strain NCIMB 40014 with 5-fluoro 2-deoxyuridine and selecting those cells which were resistant to high concentrations of this pyrimidine analogue to produce strain L-17.

Strain L-17 shows a marked ability to produce thymidine and/or thymine which products accumulate in the culture medium.

EXAMPLE 4

Production of Thymidine Using Strain L-17

The inoculation medium set out in Table 4 was prepared and was inoculated in a shake flask with a culture of strain Brevibacterium L-17 produced as described in Example 3.

TABLE 4

| Component | Concentration per l |
| --- | --- |
| 0.5 M phosphate buffer | 20 ml |
| $(NH_4)_2SO_4$ | 0.18 g |
| $MgSO_4.7H_2O$ | 0.02 g |
| $FeCl_3$ (0.972%) | 0.1 ml |
| Fisons Trace Elements Mixture | 1 ml |
| Yeast Extract | 10.00 g |

The inoculated medium was shaken at a stirrer speed of 150 rpm at a temperature of 28° C. and a pH of 7. 200 mls of the inoculated medium were thereafter transferred to a fermenter having a 3 liter working volume and the medium set out in Table 1 was added. Cultivation then took place at a pH of 7 (maintained by additions of 50% ammonium hydroxide solution), a temperature of 25° C. and under a zero dissolved oxygen tension (DOT). A stirrer speed of 500 rpm was maintained during cultivation. During cultivation the glucose concentration in the medium was monitored and a further 200 g/l was fed into the fermenter.

The product was found to contain 1.9 g/l of thymidine and 2.0 g/l of thymine.

The thymidine and the thymine produced were separated from the culture medium by ion exchange separation in the following manner:

The cells were removed from the fermenter product using a centrifuge. The liquor containing thymidine and thymine was passed onto an adsorbent column (diameter 2.6 cm, length 50 cm) packed with XAD4 resin (Rohm & Haas, Crawley, UK). The column was eluted with water pH 7 at a flow rate of 4 column volumes per hour. A thymine rich fraction was eluted in water after 5 column volumes had passed through the column. The column was then eluted with methanol. A thymidine fraction was eluted after one column volume of methanol.

EXAMPLE 5

Production of Strain 2.977

Strain 2.977 was produced by a two stage method from ATCC 19390.

In the first stage ATCC 19390 was treated with UV light and to the resulting culture was added the folate antagonist trimethoprim. Cells were selected which were resistant to trimethoprim producing strain No. 2.602. Strain No. 2.602 was thereafter cultured and treated with UV light and to the resulting culture was added 5-fluoro-2-deoxyuridine. Cells were selected which were resistant to high concentrations of 5-fluoro-2-deoxyuridine producing strain 2.977.

The production is essentially the same as that described earlier for strain L-17 (see Example 3).

I claim:

1. A process for the production of thymidine and/or thymine which comprises aerobically cultivating a thymidine and/or thymine producing bacterial strain of the genus Brevibacterium, obtained by mutagenesis and selection, in a culture medium containing an assimilable carbon source and other nutrients under suitable cultural conditions, accumulating the produced thymidine and/or thymine directly in the medium and thereafter separating the produced and accumulated thymidine and/or thymine from the medium.

2. A process according to claim 1 wherein the bacterial strain is a strain of the species *Brevibacterium helvolum*.

3. A process according to claim 2 wherein the bacterial strain is selected from the group consisting of the strains *Brevibacterium helvolum* strains NCIMB 40014, 40116 or 40117 and mutants derived from these strains.

4. A process according to claim 3 which is carried out as a batch or fed batch process.

5. A process according to claim 3 wherein the assimilable carbon source is glucose.

6. A process according to claim 3 wherein the bacterial strain is cultivated at a pH in the range 5 to 9.

7. A process according to claim 3 wherein the bacterial strain is cultivated at a temperature in the range 20° to 35° C.

8. A process according to claim 3 wherein the produced and accumulated thymidine and/or thymine is separated from the medium by ion exchange.

9. A process according to claim 8 wherein the produced and accumulated thymidine and/or thymine is adsorbed onto an ion exchange resin and eluted specifically using water and methanol.

10. A process for the production of thymidine and/or thymine which comprises aerobically cultivating a thymidine and/or thymine producing bacterial strain of the genus Brevibacterium, obtained by mutagenesis and selection, in a culture medium containing an assimilable carbon source and other nutrients under suitable cultural conditions, accumulating the produced thymidine and/or thymine directly in the medium, separating the produced and accumulated thymidine and/or thymine from the medium and thereafter purifying the separated thymidine and/or thymine.

11. Biologically pure cultures of *Brevibacterium helvolum* strain NCIMB 40014 and mutants derived therefrom.

* * * * *